United States Patent
Koehler

(10) Patent No.: US 9,299,172 B2
(45) Date of Patent: Mar. 29, 2016

(54) IMAGE GENERATION APPARATUS

(75) Inventor: Thomas Koehler, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/234,641

(22) PCT Filed: Jul. 2, 2012

(86) PCT No.: PCT/IB2012/053346
§ 371 (c)(1),
(2), (4) Date: Jan. 24, 2014

(87) PCT Pub. No.: WO2013/014554
PCT Pub. Date: Jan. 31, 2013

(65) Prior Publication Data
US 2014/0153809 A1    Jun. 5, 2014

Related U.S. Application Data

(60) Provisional application No. 61/512,451, filed on Jul. 28, 2011.

(51) Int. Cl.
*G06T 11/00* (2006.01)
*G06T 5/50* (2006.01)
*A61B 6/03* (2006.01)
(Continued)

(52) U.S. Cl.
CPC .............. *G06T 11/008* (2013.01); *A61B 6/032* (2013.01); *A61B 6/5205* (2013.01); *A61B 6/5235* (2013.01); *A61B 6/5258* (2013.01); *G06T 5/002* (2013.01); *G06T 5/50* (2013.01); *A61B 6/037* (2013.01); *A61B 6/463* (2013.01);
(Continued)

(58) Field of Classification Search
None
See application file for complete search history.

(56) References Cited

U.S. PATENT DOCUMENTS 5,182,728 A * 1/1993 Shen et al. .................. 367/7
5,909,476 A    6/1999 Cheng et al.
(Continued)

FOREIGN PATENT DOCUMENTS

DE   102008048682 A1   12/2009
WO   2006027536 A1    3/2006
WO   2011036624 A1    3/2011

OTHER PUBLICATIONS

Bockenbach, O., et al.; Real Time Adaptive Filtering for Computed Tomography Applications; 2007; IEEE Trans. on Nuclear Science; M13-281; 3077-3081.
(Continued)

*Primary Examiner* — Jon Chang

(57) ABSTRACT

The invention relates to an image generation apparatus for generating an image of an object. An image providing unit (11, 16) provides a first image of the object and a second image of the object, wherein the first image has a smaller noise level than the second image. A display window providing unit (12) provides a display window being indicative of the range of image values shown on a display (14), and a combining unit (13) generates a combination image by combining the first image and the second image depending on the window width of the provided display window. This allows considering the influence of the display window on the noise appearance. Thus, by taking into account the first image and the second image having different noise levels and the provided display window, a combined image can be generated, which has an improved noise appearance.

20 Claims, 2 Drawing Sheets

(51) Int. Cl.
*G06T 5/00* (2006.01)
*A61B 6/00* (2006.01)

(52) U.S. Cl.
CPC ...... *A61B 6/465* (2013.01); *G06T 2207/10081* (2013.01); *G06T 2207/30004* (2013.01)

(56) References Cited

U.S. PATENT DOCUMENTS

| | | | |
|---|---|---|---|
| 7,447,295 B2 | 11/2008 | Hoheisel et al. | |
| 2007/0104317 A1* | 5/2007 | Ohishi | 378/98.12 |
| 2007/0232914 A1* | 10/2007 | Chen et al. | 600/443 |
| 2009/0190814 A1 | 7/2009 | Bouman et al. | |
| 2009/0324045 A1 | 12/2009 | Grasruck et al. | |
| 2010/0014729 A1* | 1/2010 | Choi | G06T 5/50 382/131 |
| 2010/0128959 A1 | 5/2010 | Wong et al. | |

OTHER PUBLICATIONS

Coupe, P., et al.; An optimized blockwise nonlocal means denoising filter for 3-D magnetic resonance images; 2008; IEEE Trans. on Medical Imaging; 27(4)425-441.

Liu, C., et al.; Automatic Estimation and Removal of Noise from a Single Image; 2008; IEEE Trans. on Pattern Analysis and Machine Intelligence; 30(2)299-314.

Sunnegardh, J.; Combining Analytical and Iterative Reconstruction in Helical Cone-Beam CT; 2007; Linkoping Studies in Science and Technology, Thesis No. 1301. http://liu.diva-porta.org/smash/get/diva2:23125/.

Thibault, J. B., et al.; A three-dimensional statistical approach to mproved image quality for multislice helical CT; 2007; Med. Phys.; 34(11)4526-4544.

von Falck, C., et al.; Informatics in Radiology: Sliding-Thin-Slab Averaging for Improved Depiction of Low-Contrast Lesions with Radiation Dose Savings at Thin-Section CT; 2010; RadioGraphics; 30:317-326.

Wunderlich, A., et al.; Image Covariance and Lesion Detectability in Direct Fan-Beam X-Ray Computed Tomography; 2008; Phys Med Biol.; 53(10)2471-2493.

Zou, Y., et al.; Theory and algorithms for image reconstruction on chords and within regions of interest; 2005; JOSA A; 22(11)2372-2384.

* cited by examiner

IMAGE GENERATION APPARATUS

CROSS REFERENCE TO RELATED APPLICATIONS

This application is a national filing of PCT application Serial No. PCT/IB2012/053346, filed Jul. 2, 2012, published as WO 2013/014554 A1 on Jan. 31, 2013, which claims the benefit of U.S. provisional application Ser. No. 61/512,451 filed Jul. 28, 2011, which is incorporated herein by reference.

FIELD OF THE INVENTION

The invention relates to an image generation apparatus, an image generation method and an image generation computer program for generating an image of an object.

BACKGROUND OF THE INVENTION

In the field of computed tomography generally a radiation source is rotated around an object to be imaged and radiation emitted by the radiation source and having traversed the object is detected by a detector for generating projection data for different rotational positions of the radiation source with respect to the object. An image of the object can be generated from the projection data by using a reconstruction algorithm. For example, by using a filtered back-projection algorithm a relatively noisy image can be reconstructed, whereas by using an iterative reconstruction algorithm an image can be reconstructed having substantially no noise. A relatively noisy image is generally not desired, and an image having substantially no noise has an undesirable look-and-feel appearance. For instance, it may seem to be painted or flat.

SUMMARY OF THE INVENTION

It is an object of the present invention to provide an image generation apparatus, an image generation method and an image generation computer program for generating an image of an object, which allow generating an image having an improved noise appearance.

In a first aspect of the present invention an image generation apparatus for generating an image of an object is presented, wherein the image generation apparatus comprises:
an image providing unit for providing a first image of the object and a second image of the object, the first image having a smaller noise level than the second image,
a display window providing unit for providing a display window, the display window being indicative of the range of image values shown on a display, and
a combining unit for generating a combination image by combining the first image and the second image depending on the window width of provided display window.

Since the combining unit generates a combination image by combining the first image and the second image depending on the window width of the provided display window, the influence of the display window on the noise appearance can be considered. In particular, by taking into account the first image and the second image having different noise levels and the provided display window, a combined image can be generated having an improved noise appearance.

The image providing unit can be a storing unit, in which the first and second images of the object are stored already. However, the image providing unit can also be a receiving unit for receiving the first and second images from a reconstruction unit of an imaging system like a computed tomography imaging system, a nuclear imaging system, a magnetic resonance imaging system, an ultrasound imaging system, et cetera. The image providing unit can also be the reconstruction unit of the imaging system or a combination of the reconstruction unit and an acquisition unit for acquiring raw data being indicative of the object. For example, the acquisition unit can be an acquisition unit of a computed tomography system for acquiring projection data.

The image generation apparatus can be an imaging system, wherein the image providing unit is formed by an acquisition unit for acquiring raw data being indicative of the object and a reconstruction unit for reconstructing the first and second images of the object from the acquired raw data. However, the image generation apparatus can also be an image processing computer for generating a combined image based on provided first and second images, wherein the image processing computer comprises at least the image providing unit, the display window providing unit, and the combining unit.

It is preferred that the image providing unit is adapted to provide an image having been reconstructed from measured raw data being indicative of the object by using a first reconstruction method as the first image and an image having been reconstructed from the measured raw data by using a second reconstruction method as the second image. It is further preferred that the first reconstruction method is an iterative reconstruction method and the second reconstruction method is an analytical reconstruction method. In particular, the analytical reconstruction method is a filtered backprojection reconstruction method. By using an iterative reconstruction method for reconstructing the first image a first image can be reconstructed having a noise level being substantially zero. However, an image having a noise level of substantially zero may have an undesirable look-and-feel appearance. It may, for example, look painted or flat. In contrast, if the second image is reconstructed by using an analytical reconstruction method, in particular, a filtered back-projection reconstruction method, the second image can have a relatively large noise level. By using first and second images having such different noise levels, a combined image can be generated having a desired noise appearance for a relatively large range of possible window widths of display windows.

The display window is indicative of the range of image values shown on a display. If, for example, the images are computed tomography images and the image values are Hounsfield values, the display window defines the range of Hounsfield values shown on a display. The display window can be defined by a window level indicating the image value in the center of the display value and by the window width indicating the width of the display window centered at the window level.

The display window providing unit is preferentially adapted to allow a user to set a desired display window, wherein the combining unit is adapted to generate the combined image depending on the window width of the set display window. The generation of the combined image is preferentially performed in realtime such that with setting, in particular, modifying, the display window, especially with setting the window width, the combined image is re-calculated and shown on a display. The combining unit can be adapted such that the combined image is only re-calculated, if the window width is set, in particular, modified, independently of a possible modification of the window level. In an embodiment, the display window providing unit comprises a graphical user interface allowing a user to set the display window, wherein the display window providing unit is adapted to provide the set display window. For example, the graphical user interface can comprise one or several sliding elements for allowing a user to set the display window. In particular, a first sliding element can be provided for setting the window level and a second sliding element can be provided for setting the window width.

Preferentially, the combining unit is adapted to determine a first weight for weighting the first image and a second weight for weighting the second image depending on the provided display window, to weight the first image with the first weight and the second image with the second weight, and to sum the weighted first and second images. This allows, for example, fading the second image into the first image or vice versa in a relatively simple way.

It is preferred that the combining unit is adapted to combine a first amount of the first image with a second amount of the second image, if the display window is narrower, and to combine a third amount of the first image with a fourth amount of the second image, if the display window is wider, wherein the first amount is larger than the third amount and the second amount is smaller than the fourth amount. For example, if the first image is an iteratively reconstructed image and the second image is an image, which has been reconstructed by using a filtered back-projection reconstruction method, for a relatively narrow display window, only a relatively small amount of the second image should be faded into the first image, because otherwise the noise becomes too dominant. On the other hand, for a relatively wide display window a larger amount of the second image should be faded into the first image, because otherwise the noise level is so low that the resulting combined image has a flat look-and-feel appearance. By combining a larger amount of the first image with a smaller amount of the second image, if the display window is narrower, and by combining a smaller amount of the first image with a larger amount of the second image, if the display window is wider, a combined image can be generated, which does not have too dominant noise and which does not have a flat look-and-feel appearance. In other words, a combined image having desired noise can be generated, if for a narrower display window the combined image contains a relatively small amount of the second image and if for a wider display window the combined image contains a relatively large amount of the second image.

In an embodiment, the combining unit is adapted to combine the first image and the second image such that the amount of the first image decreases and the amount of the second image increases with increasing window width of the display window. In particular, the combining unit can be adapted to combine the first image and the second image such that the amount of the first image monotonically decreases and the amount of the second image monotonically increases with increasing window width of the display window. The increase and the decrease can be limited to certain regions of the window width, which can be defined by window width thresholds. For example, the combining unit can adapted such that the amount of the first image decreases and the amount of the second image increases with increasing window width of the display window, only if the window width is larger than a first threshold window width and/or smaller than a second threshold window width. For certain applications like reviewing medical images of body regions, for example, a head region or an abdomen region, the noise appearing in the combined image should not be smaller than a given noise threshold. The combining unit can therefore be adapted such that, for example, below a predefined first window width threshold, the increase of the amount of the first image having the lower noise level and the corresponding decrease of the amount of the second image having the larger noise level is stopped. The predefined window width thresholds can be application dependent. For example, for reviewing a head region the first window width threshold can be about 50 Hounsfield units and for reviewing an abdomen region the first window width threshold can be about 200 Hounsfield units.

In a further embodiment, the combining unit can be adapted to combine the first image and the second image such that the amount of the first image decreases and the amount of the second image increases with increasing window width of the display window for window widths being smaller than a third threshold window width, and to combine the first image and the second image such that the amount of the first image increases and the amount of the second image decreases with increasing window width of the display window for window widths being equal to or larger than the third threshold window width. Also in this embodiment, the increase and the decrease can be limited to certain regions of the window width, which can be defined by window width thresholds. For example, the combining unit can be adapted to combine the first image and the second image such that the amount of the first image decreases and the amount of the second image increases with increasing window width of the display window for window widths being smaller than the third threshold window width and larger than a fourth threshold window width, and/or to combine the first image and the second image such that the amount of the first image increases and the amount of the second image decreases with increasing window width of the display window for window widths being equal to or larger than the third threshold window width and smaller than a fifth threshold window width. Since the amount of the first image, which contributes to the combined image, firstly decreases in a first window width region and then increases in a second window width region with increasing window width, in the first window width region an increasing part of the second image having the larger noise level contributes to the combined image, in order to obtain a combined image having desired noise. However, if the window width becomes larger, i.e. if the window width is within the second window width region, also in the second image noise may not be visible anymore and it may be more important to provide high contrast, which may be obtained by using a larger amount of the first image having a lower noise level. Thus, by firstly decreasing the amount of the first image and then increasing the amount of the first image, a combined image having desired noise can be obtained, wherein for relative large window widths the combination of the first and second images can be performed such that the contrast is improved.

In a further aspect of the present invention an image generation method for generating an image of an object is presented, wherein the image generation method comprises:
    providing a first image of the object and a second image of the object by an image providing unit, the first image having a smaller noise level than the second image,
    providing a display window by a display window providing unit, the display window being indicative of the range of image values shown on a display, and
    generating a combination image by combining the first image and the second image depending on the window width of the provided display window by a combining unit.

In a further aspect of the present invention a computer program for generating an image of an object is presented, wherein the computer program comprises program code means for causing an image generation apparatus as defined herein to carry out the steps of the image generation method as defined herein, when the computer program is run on a computer controlling the image generation apparatus.

It shall be understood that the image generation apparatus disclosed herein, image generation method disclosed herein and the computer program disclosed herein have similar and/or identical preferred embodiments as defined herein.

It shall be understood that a preferred embodiment of the invention can also be any combination of the embodiments disclosed herein.

DETAILED DESCRIPTION OF EMBODIMENTS

Figure 1:
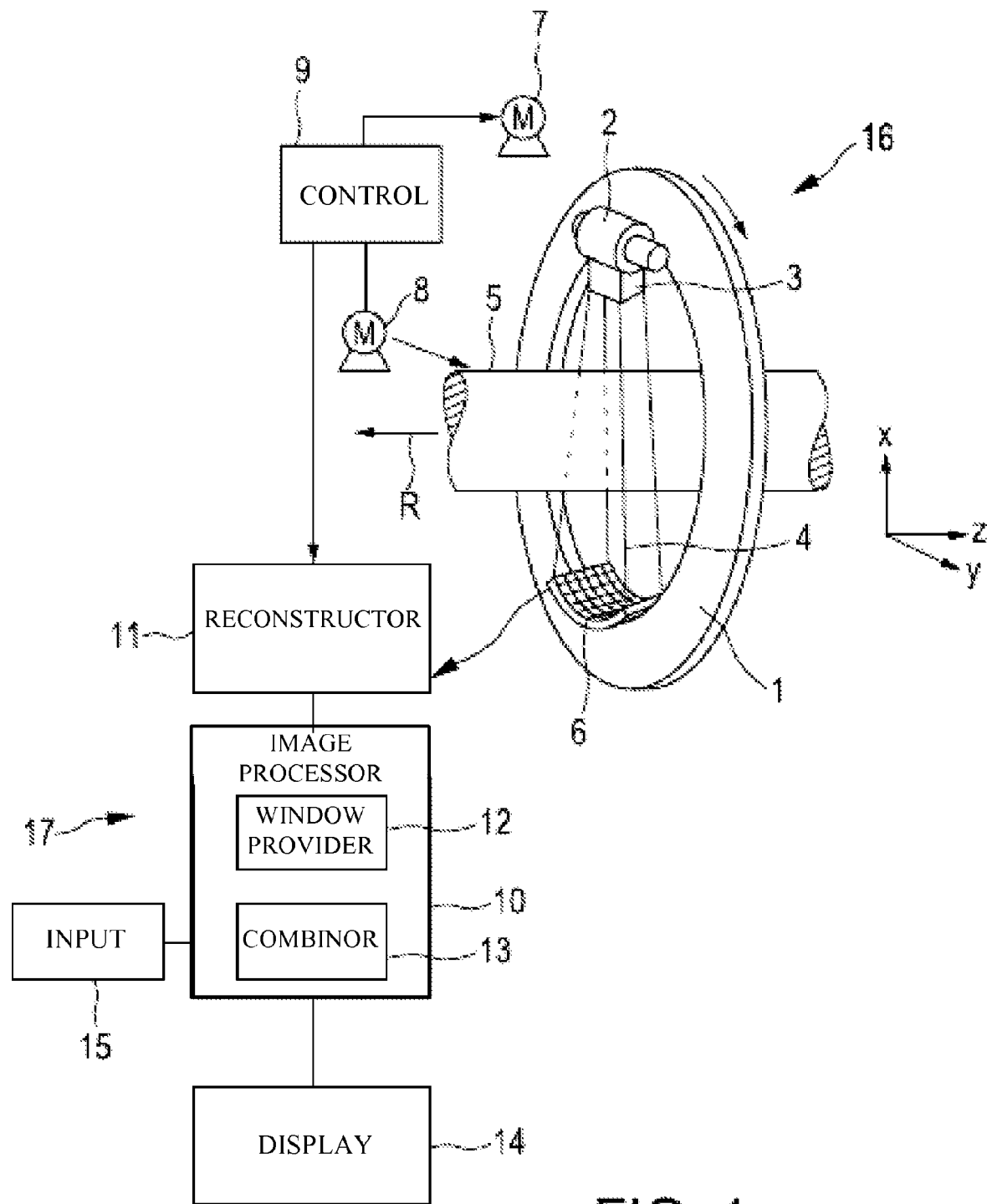
FIG. 1 shows schematically and exemplarily an embodiment of an image generation apparatus for generating an image of an object.

FIG. 1 shows schematically and exemplarily an embodiment of an image generation apparatus for generating an image of an object. In this embodiment, the image generation apparatus is a computed tomography apparatus. The computed tomography apparatus 17 includes a gantry 1 which is capable of rotation about a rotational axis R which extends parallel to a z direction. A radiation source 2, which is, in this embodiment, an x-ray tube, is mounted on the gantry 1. The radiation source 2 is provided with a collimator 3, which forms, in this embodiment, a conical radiation beam 4 from the radiation generated by the radiation source 2. The radiation traverses an object (not shown), such as a patient, in an examination zone 5 which is, in this embodiment, cylindrical. After having traversed the examination zone 5 the radiation beam 4 is incident on a detection device 6, which comprises a two-dimensional detection surface. The detection device 6 is mounted on the gantry 1.

The computed tomography apparatus comprises two motors 7, 8. The gantry 1 is driven at a preferably constant but adjustable angular speed by the motor 7. The motor 8 is provided for displacing the object, for example, a patient, who is arranged on a patient table in the examination zone 5, parallel to the direction of the rotational axis R or the z axis. The motors 7, 8 are controlled by a control unit 9, for instance, such that the radiation source 2 and the examination zone 5 and, thus, the object within the examination zone 5 move relatively to each other along a helical trajectory. However, it is also possible that the object or the examination zone 5 is not moved, but that only the radiation source 2 is rotated, i.e. that the radiation source moves along a circular trajectory relative to the object or the examination zone 5. Furthermore, in another embodiment, the collimator 3 can be adapted for forming another beam shape, in particular a fan beam, and the detection device 6 can comprise a detection surface, which is shaped corresponding to the other beam shape, in particular to the fan beam.

During a relative movement of the radiation source 2 and the examination zone 5 the detection device 6 generates measured values depending on the radiation incident on the detection surface of the detection device 6. Therefore, the radiation source 2, the elements for moving the radiation source 2 relative to the examination zone 5, in particular, the motors 7, 8 and the gantry 1, and the detection device 6 form an acquisition unit 16 for acquiring projection data being measured raw data, which are indicative of the object. The measured raw data, i.e., in this embodiment, the projection data, are provided to a reconstruction unit 11 for reconstructing an image of the object from the measured raw data. The reconstruction unit 11 is adapted to reconstruct a first image from the measured raw data using a first reconstruction method and a second image from the measured raw data using a second reconstruction method. The acquisition unit 16 and the reconstruction unit 11 can therefore be regarded as being an image providing unit for providing a first image of the object and a second image of the object.

In this embodiment, the reconstruction unit 11 is adapted to reconstruct the first image by using an iterative reconstruction method and to reconstruct the second image by using a filtered backprojection reconstruction method. The iteratively reconstructed first image is reconstructed such that it has a relatively low noise level, in particular, a noise level indicating substantially zero noise, whereas the second image, which has been reconstructed by using the filtered backprojection reconstruction method, comprises a larger noise level.

The noise level can be described as a degree of random spatial variation of image properties, in particular, as a degree of random spatial variation of image values. For example, the noise level can be defined as being a noise variance, for example, as described in the article "Image covariance and lesion detectability in direct fan-beam x-ray computed tomography" by A. Wunderlich and F. Noo, Physics in Medicine and Biology, volume 53, pages 2471 to 2493 (2008), which is herewith incorporated by reference, or the noise level may be defined as described in the article "Automatic Estimation and Removal of Noise from Single Image" by C. Liu et al., IEEE Transactions on Pattern Analysis and Machine Intelligence, volume 30, number 2, pages 299 to 314 (2008), which is also incorporated by reference. Preferentially, the noise level is defined as the square root of the noise variance.

The computed tomography apparatus 17 further comprises an image processing unit 10 having a display window providing unit 12 and a combining unit 13. The display window providing unit 12 is adapted to provide a display window being indicative of the range of image values shown on a display 14. The combining unit 13 is adapted to generate a combination image by combining the first image and the second image depending on the window width of the provided display window.

The display window providing unit 12 comprises a graphical user interface allowing a user to set the display window, wherein the display window providing unit 12 is adapted to provide the set display window. Preferentially, the graphical user interface comprises one or several sliding elements for allowing a user to set the display window. For instance, a first sliding element can be provided for setting the window level and a second sliding element can be provided for setting the window width. In this embodiment, the display window defines a range of Hounsfield values shown on the display 14. The graphical user interface can interact with an input unit 15 like a keyboard or a computer mouse for allowing a user to set the desired display window. If a user modifies the display window, the generation of the combined image can be performed in realtime such that with modifying the display window, in particular, with modifying the window width of the display window, the combined image is re-calculated and shown on the display 14.

The combining unit 13 is preferentially adapted to determine a first weight for weighting the first image and a second weight for weighting the second image depending on the provided display window, to weight the first image with the first weight and the second image with the second weight, and to sum the weighted first and second images. It is further preferred that the combining unit 13 is adapted to combine a larger amount of the first image with a smaller amount of the second image, if the display window is smaller, and to combine a smaller amount of the first image with a larger amount of the second image, if the display window is larger. That means the combining unit 13 can be adapted to combine a first amount of the first image with a second amount of the second image, if the display window is narrower, and to combine a third amount of the first image with a fourth amount of the second image, if the display window is wider, wherein the first amount is larger than the third amount and the second amount is smaller than the fourth amount.

For example, if the first image is an iteratively reconstructed image and the second image is an image, which has been reconstructed by using a filtered backprojection reconstruction method, for a relatively narrow display window, only a relatively small amount of the second image should be faded in the first image, because otherwise the noise becomes too dominant. On the other hand, for a relatively wide display window a larger amount of the second image should be faded into the first image, because otherwise the noise level is so low that the resulting combined image has a flat look-and-feel appearance. By combining a larger amount of the first image with a smaller amount of the second image, if the display window is narrower, and by combining a smaller amount of the first image with a larger amount of the second image, if the display window is wider, a combined image can be generated, which does not have a too dominant noise which does not have a flat look-and-feel appearance. In other words, a combined image having a desired noise level can be generated, if for a narrower display window the combined image contains a relatively small amount of the second image and if for a wider display window the combined image contains a relatively large amount of the second image.

For instance, for a narrow display window having a window width of about 150 Hounsfield units a fading with 40% of the second image results in a too noisy image, whereas a fading with 20% of the second image creates a descent image quality. For a larger window width of about 500 Hounsfield units a fading with 20% of the second image is insufficient to create a common look-and-feel appearance, wherein a combined image with a fading with 40% of the second image looks more descent.

In an embodiment, the combining unit is adapted to combine the first image and the second image such that the amount of the first image decreases and the amount of the second image increases with increasing window width of the display window. In particular, the combining unit can be adapted to combine the first image and the second image such that the amount of the first image monotonically decreases and the amount of the second image monotonically increases with increasing window width of the display window. The increase and the decrease can be limited to certain regions of the window width, which can be defined by window width thresholds. For example, the combining unit can be adapted such that the amount of the first image decreases and the amount of the second image increases with increasing window width of the display window, only if the window width is larger than a first threshold window width and/or smaller than a second threshold window width. For certain applications like reviewing medical images of body regions, for example, a head region or an abdomen region, the noise appearing in the combined image should not be smaller than a given noise threshold. The combining unit can therefore be adapted such that, for example, below a predefined first window width threshold, the increase of the amount of the first image having the lower noise level and the corresponding decrease of the amount of the second image having the larger noise level is stopped. The predefined window width thresholds can be application dependent. For example, for reviewing a head region the first window width threshold can be about 50 Hounsfield units and for reviewing an abdomen region the first window width threshold can be about 200 Hounsfield units.

In another embodiment, the combining unit can be adapted to combine the first image and the second image such that the amount of the first image decreases and the amount of the second image increases with increasing window width of the display window for window widths being smaller than a third threshold window width, and to combine the first image and the second image such that the amount of the first image increases and the amount of the second image decreases with increasing window width of the display window for window widths being equal to or larger than the third threshold window width. Also in this embodiment, the increase and the decrease can be limited to certain regions of the window width, which can be defined by window width thresholds. For example, the combining unit can be adapted to combine the first image and the second image such that the amount of the first image decreases and the amount of the second image increases with increasing window width of the display window for window widths being smaller than the third threshold window width and larger than a fourth threshold window width, and/or to combine the first image and the second image such that the amount of the first image increases and the amount of the second image decreases with increasing window width of the display window for window widths being equal to or larger than the third threshold window width and smaller than a fifth threshold window width.

The combination image generated by the combining unit 13 is provided to the display 14 for displaying the combination image.

The reconstruction unit 11 and the image processing unit 10 can be controlled by the control unit 9.

Figure 2:
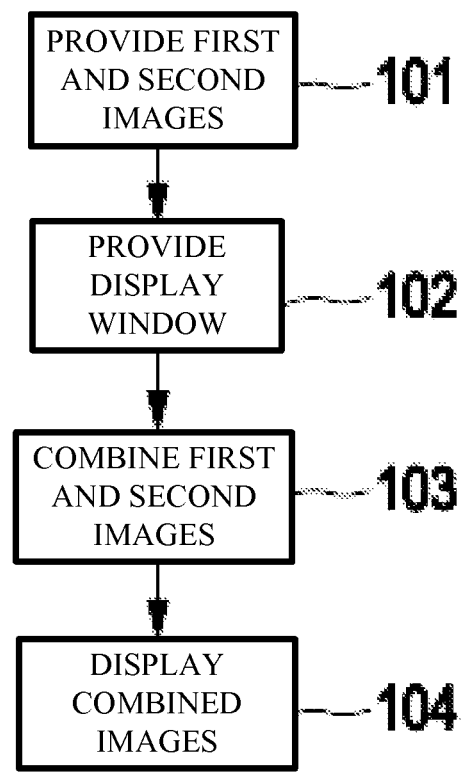
FIG. 2 shows schematically and exemplarily an embodiment of an image generation method for generating an image of an object.

In the following an embodiment of an image generation method for generating an image of an object will exemplarily be described with reference to a flowchart shown in FIG. 2.

In step 101, a first image of the object and a second image of the object are provided by the image providing unit, wherein the first image has a smaller noise level than the second image. In particular, projection data are acquired by using the acquisition unit 16 and the first and second images are reconstructed by the reconstruction unit 11, wherein the first image is reconstructed by using an iterative reconstruction method and the second image is reconstructed by using a filtered backprojection reconstruction method.

In step 102, a display window is provided by a display window providing unit 12, wherein the display window is indicative of the range of image values shown on the display 14. For example, the display window providing unit 12 can provide a graphical user interface comprising, for instance, a sliding element, allowing a user to set a desired display window, in particular, a desired window width.

The combining unit 13 combines the first image and the second image depending on the window width of the provided display window in step 103. And, in step 104, the resulting combination image is shown on the display 14.

Iterative reconstruction techniques can be used as an option to reduce the x-ray dose during a computed tomography scan. For instance, the noise level in low dose scans can be reduced almost to zero using iterative reconstruction. However, these images have an undesirable look-and-feel appearance, in particular, they seem to be painted and/or flat. The above described image generation apparatus allows therefore adjusting the amount of the second image, in particular, of the filtered backprojection image, that is faded into the first image, in particular, into the iterative reconstruction image, according to the current setting of the display window.

The iterative reconstruction method is, for example, the Iterative Coordinate Descent (ICD) method as disclosed in, for example, the article "A three-dimensional statistical approach to improved image quality for multislice helical CT" by J.-B. Thibaut et al., Medical Physics 34 (11), pages 4526 to 4544 (2007), which is herewith incorporated by reference. However, also another iterative reconstruction method can be used.

Although in the above described embodiment the image providing unit is a combination of an acquisition unit and a reconstruction unit, in other embodiments the image providing unit can also be, for example, a storing unit, in which the first and second images of the object are stored already, or a receiving unit for receiving the first and second images from a reconstruction unit of an imaging apparatus like a computed tomography imaging apparatus, a nuclear imaging apparatus, a magnetic resonance imaging apparatus, an ultrasound imaging apparatus, et cetera. The image providing unit can also be the reconstruction unit of the respective imaging system.

Although in the above described embodiment the image generation apparatus is a computed tomography imaging system, the image generation apparatus can also be just an image processing computer for generating the combined image based on provided first and second images, wherein the image processing computer comprises at least the image providing unit including a storing unit and/or a receiving unit, the display window providing unit, and the combining unit.

Although in the above described embodiment the second image is reconstructed from the projection data by using a filtered backprojection reconstruction algorithm, in other embodiments also another analytical reconstruction method can be used for reconstructing the second image. For example, the backprojection-filtration (BPF) method as described in, for instance, the article "Theory and algorithms for image reconstruction of chords and within regions of interest" by Y. Zou et al., Journal of the Optical Society of America A, volume 22, number 11, pages 2372 to 2384 (2005), which is herewith incorporated by reference, can be used for reconstructing the second image.

Although in the above descript embodiments the first image is reconstructed by using an iterative reconstruction method and the second image is reconstructed by using an analytical reconstruction method, the images having different noise levels can also be generated by using other methods. For example, an image can be provided, which may have been reconstructed by using a filtered back-projection method, and this image can be denoised by using a known denoising algorithm such that the further image comprises a lower noise level than the initially provided image. The denoised image can then be regarded as being the first image and the initial image can be regarded as being the second image. For denoising the initially provided image a known denoising algorithm can be used like the denoising algorithm disclosed in the article "An Optimized Blockwise Nonlocal Means Denoising Filter for 3-D Magnetic Resonance Images" by P. Coupé et al., IEEE Transactions on Medical Imaging, volume 27, number 4, pages 425 to 441 (2008), which is herewith incorporated by reference, or another denoising algorithm can be used.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single unit or device may fulfill the functions of several items recited in the claims. The mere fact that certain measures are recited in mutually different dependent claims does not indicate that a combination of these measures cannot be used to advantage.

Calculations like the reconstructions of the first and second images and the combining procedure for combining the first and second images performed by one or several units or devices can be performed by any other number of units or devices. For example, the reconstruction performed in step 101 and the generation of the combination image performed in step 103 can be performed by a single unit or by any other number of different units. The calculations and/or the control of the image generation apparatus in accordance with the image generation method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An image generation apparatus for generating an image of an object, the image generation apparatus comprising:
   an image providing unit for providing a first image of the object and a second image of the object, the first image having a smaller noise level than the second image,
   a display window providing unit for providing a display window, the display window indicating the range of image values shown on a display, and
   a combining unit for generating a combination image by combining the first image and the second image depending on the window width of the provided display window.

2. The image generation apparatus as defined in claim 1, wherein the image providing unit is adapted to provide an image having been reconstructed from measured raw data being indicative of the object by using a first reconstruction method as the first image and an image having been reconstructed from the measured raw data by using a second reconstruction method as the second image.

3. The image generation apparatus as defined in claim 2, wherein the first reconstruction method is an iterative reconstruction method and the second reconstruction method is an analytical reconstruction method.

4. The image generation apparatus as defined in claim 1, wherein the display window providing unit comprises a graphical user interface allowing a user to set the display window, wherein the display window providing unit is adapted to provide the set display window.

5. The image generation apparatus as defined in claim 1, wherein the combining unit is adapted to:
   determine a first weight for weighting the first image and a second weight for weighting the second image depending on the provided display window,
   weight the first image with the first weight and the second image with the second weight, and
   sum the weighted first and second images.

6. The image generation apparatus as defined in claim 1, wherein the combining unit is adapted to combine a first amount of the first image with a second amount of the second image, if the display window is narrower, and to combine a third amount of the first image with a fourth amount of the second image, if the display window is wider, wherein the first amount is larger than the third amount and the second amount is smaller than the fourth amount.

7. The image generation apparatus as defined in claim 6, wherein the combining unit is adapted to combine the first image and the second image such that the amount of the first image decreases and the amount of the second image increases with increasing window width of the display window.

8. The image generation apparatus as defined in claim 7, wherein the combining unit is adapted to combine the first image and the second image such that the amount of the first image monotonically decreases and the amount of the second image monotonically increases with increasing window width of the display window.

9. The image generation apparatus as defined in claim 7, wherein the combining unit adapted such that the amount of the first image decreases and the amount of the second image increases with increasing window width of the display window only if the window width is larger than a first threshold window width.

10. The image generation apparatus as defined in claim 7, wherein the combining unit is adapted such that the amount of the first image decreases and the amount of the second image increases with increasing window width of the display window only if the window width is smaller than a second threshold window width.

11. The image generation apparatus as defined in claim 1, wherein the combining unit adapted to combine the first image and the second image such that the amount of the first image decreases and the amount of the second image increases with increasing window width of the display window for window widths being smaller than a third threshold window width, and to combine the first image and the second image such that the amount of the first image increases and the amount of the second image decreases with increasing window width of the display window for window widths being equal to or larger than the third threshold window width.

12. The image generation apparatus as defined in claim 11, wherein the combining unit is adapted to combine the first image and the second image such that the amount of the first image decreases and the amount of the second image increases with increasing window width of the display window for window widths being smaller than the third threshold window width and larger than a fourth threshold window width, and to combine the first image and the second image such that the amount of the first image increases and the amount of the second image decreases with increasing window width of the display window for window widths being equal to or larger than the third threshold window width.

13. The image generation apparatus as defined in claim 11, wherein the combining unit is adapted to combine the first image and the second image such that the amount of the first image decreases and the amount of the second image increases with increasing window width of the display window for window widths being smaller than the third threshold window width, and to combine the first image and the second image such that the amount of the first image increases and the amount of the second image decreases with increasing window width of the display window for window widths being equal to or larger than the third threshold window width and smaller than a fifth threshold window width.

14. An image generation method fir generating an image of an object, the image generation method comprising:
providing a first image of the object and a second image of the object by an image providing unit, the first image having a smaller noise level than the second image,
providing a display window by a display window providing unit, the display window configured to indicate the range of image values shown on a display, and
generating a combination image by combining the first image and the second image depending on the window width of the provided display window by a combining unit.

15. A non-transitory computer readable medium encoded with a computer program, which, when executed by a computer processor, causes the computer processor to:
provide a first image of an object and a second image of the object by an image providing unit, the first image having a smaller noise level than the second image,
provide a display window by a display window providing unit, the display window configured to indicate the range of image values shown on a display, and
generate a combination image by combining the first image and the second image depending on the window width of the provided display window by a combining unit.

16. The image generation method as defined in claim 14, further comprising:
providing an image having been reconstructed from measured raw data being indicative of the object by using a first reconstruction method as the first image and an image having been reconstructed from the measured raw data by using a second reconstruction method as the second image.

17. The image generation method as defined in claim 16, wherein the first reconstruction method is an iterative reconstruction method and the second reconstruction method is an analytical reconstruction method.

18. The image generation method as defined in claim 14, wherein the display window providing unit comprises a graphical user interface allowing a user to set the display window, wherein the display window providing unit is adapted to provide the set display window.

19. The image generation method as defined in claim 14, further comprising: determining a first weight for weighting the first image and a second weight for weighting the second image depending on the provided display window,
weighting the first image with the first weight and the second image with the second weight, and
summing the weighted first and second images.

20. The image generation method as defined in claim 14, further comprising:
combining a first amount of the first image with a second amount of the second image, if the display window is narrower, and
combining a third amount of the first image with a fourth amount of the second image, if the display window is wider,
wherein the first amount is larger than the third amount and the second amount is smaller than the fourth amount.

* * * * *